Figure 1:
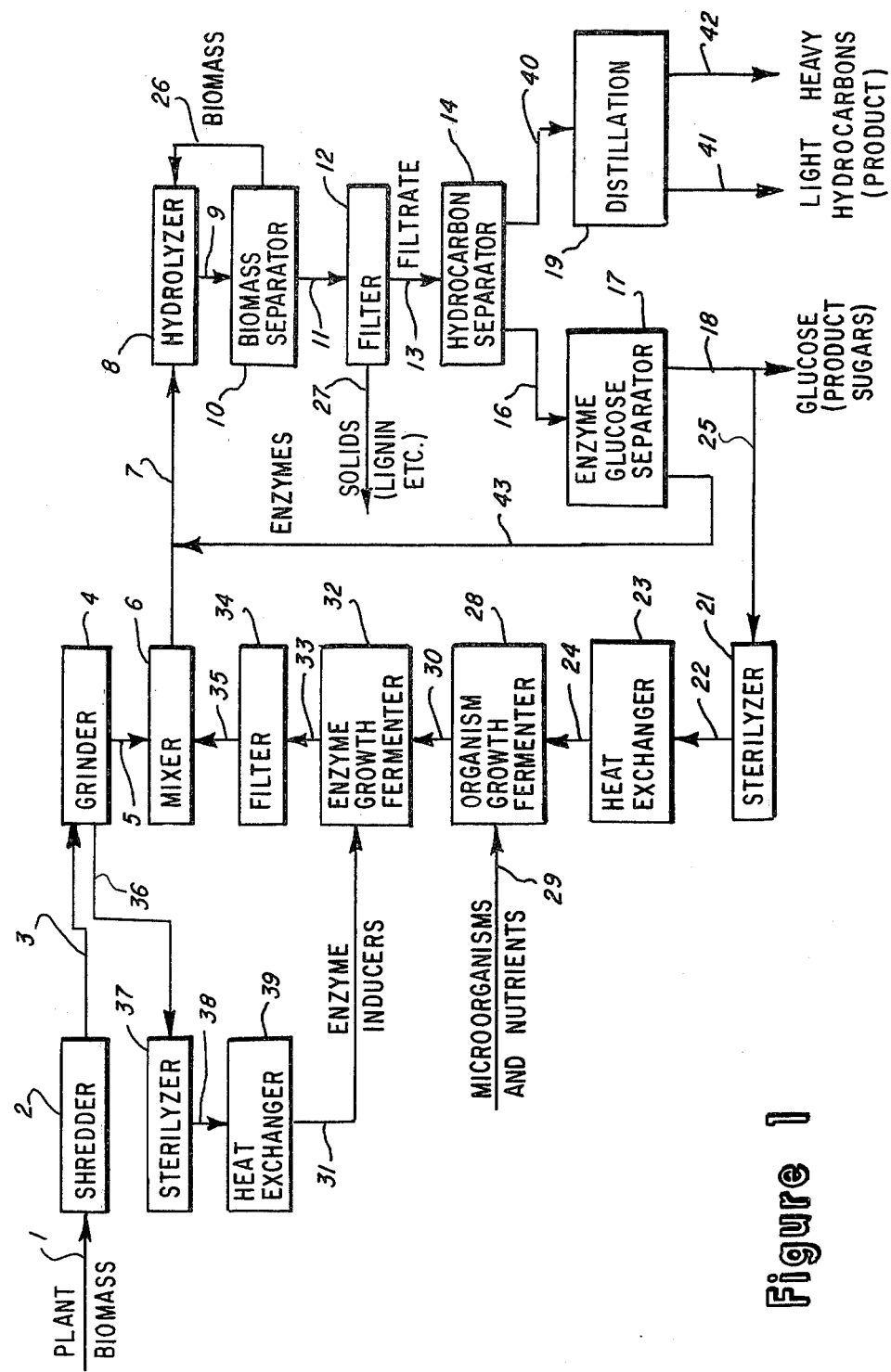

United States Patent [19]

Weil et al.

[11] 4,338,399

[45] Jul. 6, 1982

[54] PROCESS FOR RECOVERING HYDROCARBONS FROM HYDROCARBON-CONTAINING BIOMASS

[75] Inventors: Thomas A. Weil, Naperville; Peter M. Dzadzic, Lisle, both of Ill.; Chien-Cheng J. Shih, Irvine, Calif.; Michael C. Price, West Chicago, Ill.

[73] Assignee: Standard Oil Company (Indiana), Chicago, Ill.

[21] Appl. No.: 187,492

[22] Filed: Sep. 15, 1980

[51] Int. Cl.³ .................... C12P 19/14; C12P 19/02; C12P 5/00; C12P 5/02

[52] U.S. Cl. ..................................... 435/99; 435/105; 435/166; 435/167; 435/267; 435/813

[58] Field of Search .................. 435/99, 105, 166–171, 435/262, 267, 271, 276, 813, 819; 426/7, 49, 50, 52

[56] References Cited

U.S. PATENT DOCUMENTS

| | | | |
|---|---|---|---|
| 1,839,191 | 1/1932 | Ambros et al. | 435/267 |
| 2,440,554 | 4/1948 | Waghski et al. | 435/267 |
| 2,453,858 | 11/1948 | Porges et al. | 435/267 |
| 3,972,775 | 8/1976 | Wilke et al. | 435/813 |

OTHER PUBLICATIONS

Nielson, et al. "Plant Crops as a Source of Fuel and Hydrocarbon-like Materials", Science, vol. 198, (1977), pp. 942–944.
Buchanan, et al. "Hydrocarbon—and Rubber–Producing Crops Evaluation of 100 U.S. Plant Species", Chem. Abstracts, vol. 90, (1979), p. 308, abs. No. 3150t.

Primary Examiner—Thomas G. Wiseman
Attorney, Agent, or Firm—William C. Clarke; William T. McClain; William H. Magidson

[57] ABSTRACT

A process for enzymatically converting whole plant biomass containing hydrocarbon-containing laticifers to soluble sugars and recovering hydrocarbons in increased yields which comprises hydrolyzing whole plant cellulosic material in the presence of enzymes, particularly cellulase, hemicellulase, and pectinase, to produce a hydrocarbon product and recovering from the hydrolysis products a major proportion of the cellulase, hemicellulase and pectinase enzymes for reuse. At least some portion of the required make-up of cellulase, hemicellulase and pectinase enzymes is produced in a two-stage operation wherein, in the first stage, a portion of the output sugar solution is used to grow enzyme secreting microorganisms selected from the group consisting of cellulase-secreting microorganisms, hemicellulase-secreting microorganisms, pectinase-secreting microorganisms, and mixtures thereof, and in the second stage, cellulase, hemicellulase and pectinase enzyme formation is induced in the microorganism-containing culture medium by the addition of an appropriate inducer such as biomass. The cellulase, hemicellulase and pectinase enzymes are then recycled for use in the hydrolysis reaction.

5 Claims, 1 Drawing Figure

PROCESS FOR RECOVERING HYDROCARBONS FROM HYDROCARBON-CONTAINING BIOMASS

BACKGROUND OF THE INVENTION

This invention relates to the recovery of hydrocarbons from hydrocarbon-containing plants by enzymatic degradation of cellulosic materials, particularly laticifer cells found in latex-containing plants. Laticifers are plant cells which contain latex.

Considerable effort has been directed toward the development of renewable energy resources to alleviate dependence on fossil fuel. Attention has been focused on the direct production of hydrocarbons from plants wherein biosynthesis of terpenes and related compounds occur. Representative of the terpenes, hydrocarbons of various degrees of polymerization, are the lower terpenes as essential oils, and the higher terpenes, as carotenoids, saponins, and rubber. These materials are held within plant cells composed of cellulose, hemicellulose, pectins, and other materials. The various rubber plants yield their rubber product as a latex which contains various substances in solution and in colloidal suspension. Of the approximately 1,800 species of plants reported to contain rubber, only a few yield enough rubber to make them commercially useful. For example, in Hevea, rubber may constitute 40 to 50% of the latex.

Many early efforts to recover the hydrocarbons contained in plants were geared to such activities as tapping of rubber trees, distillation of pine stumps to obtain hydrocarbon resins, or as byproduct recovery from such activities as sulfate pulping. The crushing of oil seeds to obtain vegetable oils is well-known. Crushing combined with water extraction as well as catalytic processes are known. For example, U.S. Pat. No. 1,740,079 teaches the extraction of rubber from plants such as guayule. The guayule plants are reaped and dried, then crushed by rolls or other suitable machinery so as to open up the pith seams and break the bark. The crushed plants are cut into short pieces and soaked in water until the bark and pith are soft. The entire mass of material is then introduced into a water-filled ball mill and subjected to the action of such mill until the bark and pithy material are separated from the hard woody material. The bark and pithy material are reduced to a pulp. The rubber particles are freed from the rest of the material and are agglomerated to rise to the surface of the water for removal. Another extraction process for recovering hydrocarbon values from whole-plant feedstock crops employs rolling mills that shear and compress plant material between dissynchronous rollers. The action of the rollers ruptures cellular material to facilitate downstream extraction with solvents in contrast to the conventional process in use which is wet milling (*Chemical Engineering*, Sept. 11, 1978, p. 101). Catalytic processes also have been developed. Hydrolyzed wood chips are converted directly to an oil by means of a sodium carbonate catalyst. (*Chemical and Eng. News*, Oct. 1, 1979, p. 35). Methods have been suggested to recover certain useful hydrocarbons from plant crops such as solvent extraction of organic materials (*Science*, 198, Dec. 2, 1977, 942–944), pyrolysis of tree bark to obtain benzene compounds (*Tr. Sib. Tekhnol. Inst.*, 1979, No. 43, 30–33; CA77:90240v), and hydrolysis of carbohydrates in plant biomass to sugars for further processing (*Chemical and Eng. News*, Apr. 3, 1978, p. 31).

In recent years, cellulose degradation through enzymatic means has been a subject of investigation by various workers. U.S. Pat. No. 3,616,222 teaches use of mixed cultures of enzymes in a process for saccharification of cellulose to increase the rate of converting cellulose to sugar. U.S. Pat. No. 3,812,012 to Buschmann, et al., teaches a method for degrading natural plant material with an enzyme preparation containing pectic acid trans-eliminase as the effective ingredient. Buschmann '012 teaches that while it is known to add pectin hydrolases to digestive preparations to degrade plant material, pectin hydrolases can be very active against soluble pectins but can be less active on genuine plant materials which are chemically and physically linked with other polysaccharide components and therefore differ from the isolated soluble pectins in biochemical properties. U.S. Pat. No. 3,972,775 teaches a process for the conversion of cellulosic materials to sugar in the presence of cellulase enzymes wherein a portion of the cellulase enzyme is recovered for reuse and some of the makeup enzyme is produced in a two-stage operation. U.S. Pat. No. 3,990,944 teaches manufacture of alcohol from cellulosic materials by a one-step process involving the simultaneous reaction of a cellulosic material, a cellulase and an alcohol-producing microorganism. U.S. Pat. No. 3,990,945 teaches a process for enzymatic hydrolysis of cellulose to obtain water-soluble sugars wherein the enzyme source is an aqueous culture mass from which the enzyme is not separated, thereby increasing hydrolysis rates and yields of water-soluble sugars. U.S. Pat. No. 4,009,075 teaches a process for making alcohol from sterilized cellulosic material using cellulase enzyme and yeast. Sterilization eliminates unwanted bacterial strains and aids reaction speeds by causing a partial breakdown of cellulosic fibers. U.S. Pat. No. 4,089,745 teaches a process for enzymatically converting cellulose from corn hulls to glucose. Alkali is used to first liberate cellulose from the corn hulls. U.S. Pat. No. 4,094,742 teaches production of ethanol from cellulose through the combined growth of thermophilic cellulytic sparocytophaga and an ethanol-producing thermophilic bacillus. An alkali or acid treatment degrades lignin sufficiently to make the cellulose available for contact with the mixed culture. U.S. Pat. No. 4,097,333 teaches increased production of glucose from ethylene-treated cellulose. Yields are low without ethylene treatment because of the stranded and crystalline nature of cellulose.

Accordingly, the prior art teaches a number of processes for production of glucose from cellulose in the presence of lignin. Crushing and extraction processes for hydrocarbon-containing plants have also been taught. However, prior art processes have not dealt with the problem of obtaining hydrocarbons from hydrocarbon-containing plants wherein the hydrocarbon content is low and is contained in laticifer cells.

An object of this invention accordingly is to provide a process for production and recovery of hydrocarbons from hydrocarbon-containing plants which permits the effective utilization of whole plant biomass as a raw material source. Another object of this invention is to provide a process for production of liquid hydrocarbons in quantity from plant biomass. Another object of this invention is to provide a process for degradation of cellulose to provide glucose and to break the cellulosic walls of latex-containing cells, thereby releasing hydrocarbon-containing latex and increasing hydrocarbon yields. Another object is to provide increased production of hydrocarbons from renewable natural resources.

These and other objects and advantages will become clear from the following specification.

SUMMARY OF THE INVENTION

A process for enzymatically converting whole plant biomass containing hydrocarbon-containing laticifers to soluble sugars and recovering hydrocarbons in increased yields.

DETAILS OF THE INVENTION

The invention relates to a process for producing sugars and recovering hydrocarbons contained in laticifers of whole plant biomass which are rich in hydrocarbons. Examples of these plants are *Euphorbia heterophylla, Euphorbia lathyrus, Euphorbia marginata, Asclepias syriaca, Calotropis procera, Parthenium Argentatum* (guayule) and *Apocynum sibiricum*. The invented process is not limited to these plants and can be applied to any hydrocarbon-containing plant including those in the Euphorbiaceae, Apocynaceae, Asclepiadaceae, Compositae, Cactaceae, and Pinaceae families. The plant material can be used fresh, frozen or dry. Enzymes which are effective include the cellulases, hemicellulases, maceraces and pectinases and combinations thereof. Either the isolated enzyme or the living enzyme producing culture can be used. A number of enzymes have been isolated from fungi and bacteria which hydrolyze cellulose and hemicellulose to simple sugars and degrade pectins including enzymes from the microorganisms: *Trichoderma viride, Tricoderma koningi, Asperigillus niger, Asperigillus oryzae, Asperigillus flavus, Basidiomycetes poria,* thermophilic fungi and/or bacteria such as *Clostridium thermocellum* and others. The commercially available enzymes produced by cultures of *Trichoderma viride* and *Aspergillus niger*, which include those from Miles Laboratories, Rohm and Haas, Kinki Yokult, G. B. Fermentation, Calbiochem-Behring, and Aldrich are particularly useful. The reaction can be run with or without mixing, preferably at a temperature between 30° and 60° C. although temperatures of 10° to 90° C. can be used. The reaction is run in an aqueous buffered solution preferably at pH 5 although a pH range from 0 to 10 is acceptable. Reaction times of from 1 to 2 hours up to several hundred hours can be used depending on enzyme concentration, temperature, mixing rate and pH. Enzyme to substrate ratios of less than $10^{-3}$ to 10 can be used. The process may be carried out in either a batch or continuous type operation. For a batch operation a reaction vessel is charged with the enzyme, plant material and solvent, and the reaction run at a particular temperature for a selected time. Following the reaction the contents of the reactor are distilled to recover hydrocarbons. The sugars produced from the cellulase and hemicellulase hydrolysis are easily recovered from the aqueous solution. For continuous operation either a plug flow or back mixed reactor is suitable.

Accordingly, the present invention is directed to a process for the enzymatic conversion of pulverized biomass wherein the lignocellulose material is treated with acid or base sufficiently to adjust the pH to maximize enzyme activity, the cellulosic and hemicellulosic content is converted to sugars in sufficient quantity to break the biomass cell walls, and/or, alternatively, pectin hydrolases are present in sufficient quantity to contribute to the digestive degradation of the cell walls, the hydrocarbon content of said biomass contained in laticifers is recovered, and makeup stream of enzymes selected from the group consisting of cellulase enzymes, hemicellulase enzymes, pectinase enzymes, and mixtures thereof, is provided by growing enzyme synthesizing microorganisms selected from the group consisting of cellulase-synthesizing microorganisms, hemicellulase-synthesizing microorganisms, pectinase-synthesizing microorganisms and mixtures thereof in a portion of the biomass substrate containing cellulosic, hemicellulosic and pectinic materials from partially degraded excess biomass.

FIG. 1 is a schematic illustration of the invention according to which sugars are produced (mainly glucose) from biomass and hydrocarbons are recovered from hydrocarbon-containing biomass by hydrolyzing the said biomass in the presence of enzymes to produce hydrocarbons composed of aliphatic, aromatic, and functionalized compounds containing nitrogen and oxygen.

Referring to FIG. 1, the whole-plant biomass is introduced by line 1 into shredder 2 and then discharged via line 3 into grinder 4 where it is ground to a suitable particle size if necessary. The ground biomass is then fed to a mixing stage 6 by line 5 where aqueous filtrate containing enzymes selected from the group consisting of cellulase enzymes, hemicellulase enzymes, pectinase enzymes and mixtures thereof from the product stream by line 35 mixes with the incoming fresh biomass. The enzyme-biomass mix is then transported by line 7 to the hydrolyzer 8. The hydrolyzer comprises a number of digesters. The hydrolysis conditions are conventional. These conditions usually involve an aqueous medium on the acid side having a pH in the range of from about 4 to 6 with 5 being preferable, a temperature in the range of about 25° C. to about 90° C., preferably 30° C. to 50° C., a cellulasic enzyme complex concentration, and/or a hemicellulase enzyme concentration and/or a pectinase enzyme complex concentration and mixtures thereof of from about 0.01 to 5 percent by weight of the reaction mixture and a cellulosic substrate concentration of from about 1 to 30 percent by weight. The amount of time required for hydrolysis depends upon the concentration of the enzyme present. The upper limit of enzyme concentration is determined by solubility of the enzymes in the solution while the lower limit is determined by maximum process times desired. The number of digesters will be determined by the physical quantity of biomass handled.

Following hydrolysis, the effluents are discharged by line 9 to biomass separator 10 wherein the aqueous glucose-containing filtrate and hydrocarbon phase are separated from the biomass solids phase. The aqueous glucose-containing filtrate and the liquid hydrocarbons from 10 are fed by line 11 to filter 12 wherein solids (lignin, etc.) in the filtrate are removed as separate products to prevent a buildup of these materials in the process streams. Aqueous filtrate containing sugars including glucose, water and hydrocarbons is fed by line 13 to hydrocarbon separator 14 wherein the aqueous glucose filtrate is removed and fed to enzyme/glucose separator 17 by line 16. Sugar product including glucose is removed from the enzyme/glucose separator by line 18. Enzyme extract from the enzyme/glucose separator is fed by line 43 to line 7 for return to hydrolyzer 8. Biomass from separator 10 is returned to hydrolyzer 8 by line 26. Solids from filter 12 containing lignin and other by product materials are removed by line 27 for use as fuel or for other utilization. Hydrocarbons from hydrocarbon separator 14 are transferred by line 40 to distillation column 19 wherein the hydrocarbons are separated into light hydrocarbon products and heavy hydrocarbon products and are removed from the process by lines 41 and 42.

A portion of the glucose product removed by line 18 from enzyme/glucose separator 17 is fed by line 25 to sterilizer 21 to serve as growth medium to maintain the cycle. In the sterilizer 21, the growth medium is heated to a suitably high temperature, for example, by heat exchange with condensing steam. Heating to a temperature of about 145° C. will effectively sterilize the growth medium. Sterile growth medium is fed to heat exchanger 23 by line 22 to cool the growth medium to a suitable temperature to permit fermentation to take place. Heat exchange can be with hydrocarbons from hydrocarbon separator 14 to heat the hydrocarbons prior to distillation in column 19. The fermentation reaction is carried out at a temperature from about 20° C. to about 50° C., preferably about 30° C. The sterilized growth medium is fed to organism growth fermenter 28 by line 24. Microorganisms and required nutrients are added by line 29 to fermenter 28. Suitable producing microorganisms such as *Trichoderma viride* are well-known (*J. Bacteriol.*, 72, 269 (1957); ibid, 79, 816 (1960); ibid, 83, 400 (1963); *Adv. In Chem. Ser.*, 95, 391 (1969)). The growth medium is held in fermenter 28 for a period of time sufficient to exhaust the nutrients for the cellulase, hemicellulase and pectinase-secreting microorganisms. Broth from fermenter 28 is fed to enzyme growth fermenter 32 by line 30 to which enzyme inducers have also been added by line 31. Enzyme inducers comprise biomass taken from grinder 4 by line 36 to sterilizer 37 to heat exchanger 39 by line 38. The presence of suitable cellulose, hemicellulose and pectin materials is required to induce formation of the cellulase, hemicellulase and pectinase enzymes. These materials can be of any source but sterilized fresh biomass material from grinder 4 is suitable. An amount sufficient to provide a cellulose concentrate of about 0.3–1.5% by weight and/or a pectin concentrate of about 0.2 to 5.0% by weight in fermenter 32 is preferred. Following enzyme production, solids are removed in filter 34, being fed by line 33. Aqueous enzyme solution from filter 34 is transferred by line 35 to mixer 6.

The cellulolytic enzyme complex utilized in the enzymatic hydrolysis of cellulose in accordance with this invention is one capable of degrading native cellulose. As such, it contains the so-called $C_1$ and $C_2$ components described by Mandels et al. in U.S. Pat. No. 3,764,475 and in an article in *Biotechnology and Bioengineering*, XVI, 1471 (1974). As is known in the art, these enzyme complexes are elaborated by such known and publicly available cellulolytic microorganisms as *Trichoderma viride, Trichoderma koningii, Fusarium solani, Fusarium javanicum*, and the like. Typical strains are *T. viride* QM6a, (ATCC 13,631), *T.koningii* (ATCC 18,649), *F.solani* (ATCC 16,372) and *F.javanicum* (ATCC 22,403). *T.viride* QM9123 (ATCC 24,449) and *T.viride* QM9414 (ATCC 26,921) are preferred. As used herein, the term "cellulolytic microorganism" means a microorganism which generates a cellulolytic enzyme complex capable of degrading native, crystalline cellulose.

Commercially available cellulase enzymes are available from Rohm and Haas, Industrial Chemicals Department, Philadelphia, Pa.; G. B. Fermentation Industries, Des Plaines, Ill.; Miles Laboratories, Inc., Marschall Division, Elkhart, Ind.; Novo Laboratories, Inc., Wilton, Conn.

Commercially available cellulase enzymes typically contain hemicellulase enzymes as well as cellulase enzymes. As used herein, the term "cellulase" accordingly encompasses "hemicellulase" also.

In summary, the process of this invention is a process using enzymes for enzymatically converting whole plant biomass containing hydrocarbon-containing laticifers to soluble sugars and recoverying hydrocarbons in increased yields which comprises (a) hydrolyzing whole plant biomass material in the presence of enzymes selected from the group consisting of cellulase, hemicellulase, pectinase enzymes and mixtures thereof under conditions which promote conversion of cellulose and hemicellulose to soluble sugars; (b) removing a stream of hydrolysis products comprising a liquid sugar containing phase, a liquid hydrocarbon containing phase and a solid phase containing unhydrolyzed spent solids, all phases containing enzymes selected from the group consisting of cellulase, hemicellulase and pectinase enzymes and mixtures thereof from the hydrolysis stage; (c) separating liquid phases and solid phases of step (b) above; (d) continuously adding a stream to step (a) of fresh hydrocarbon-containing plant biomass to replenish said whole plant biomass material converted to hydrolysis products; (e) separating said liquid phases from step (c) thereby recovering said enzymes present and said hydrocarbons present; (f) recovering a stream of product sugar solution and enzyme solution from step (e); (g) sterilizing a sugar product stream from step (f) to serve as sterile growth medium for microorganisms; (h) adding the recovered solids from step (c) to the hydrolysis stage; (i) providing a stream of makeup enzymes selected from the group consisting of cellulase, hemicellulase, pectinase enzymes and mixtures thereof for the hydrolysis steps by the steps including (1) in a first zone, growing in a suitable medium enzyme-synthesizing organisms selected from the group consisting of cellulase-synthesizing microorganisms, hemicellulase-synthesizing microorganisms, pectinase-synthesizing microorganisms and mixtures thereof, said microoganism-containing medium comprising minor portions of the product solutions; (2) in a second zone contacting said microorganism-containing medium with an amount of cellulosic, hemicellulosic and pectinic materials in an amount sufficient to induce formation of cellulase, hemicellulase and pectinase enzymes under conditions substantially nonsupportive of growth of the cellulase, hemicellulase and pectinase secreting microorganisms. The said enzymes can also consist essentially of cellulase enzymes and hemicellulase enzymes and mixtures thereof. The said whole plant biomass can comprise hydrocarbon-containing plants selected from the Euphorbiaceae, Apocynaceae, Asclepiadaceae, Compositae, Cactaceae and Pinaceae families and mixtures thereof. The said whole plant biomass can comprise hydrocarbon-containing plants selected from the group consisting of *Euphorbia heterophylla, Euphorbia lathyrus, Euphorbia marginata, Euphorbia tirucalli, Ascelpias syriaca, Calotropis procera, Parthenium argentatum, Apocynum sibiricum*, and mixtures thereof. The said enzymes can comprise enzymes from the microorganisms *Trichoderma viride, Aspergillus niger, Basidiomycetes poria, Trichoderma koningii, Fusarium soloni, Clostriduim thermocellum, Fusarium javanicum* and mixtures thereof. The process can be batch or continuous.

Embodiments of the present invention can be found in the following examples. These embodiments and examples are presented for purposes of illustration only and are not intended to limit the scope of the invention.

EXAMPLE I

The following simulates a batch process for recovery of hydrocarbons from latex-containing plants without the use of enzymes.

A 33.2 g portion of *Euphorbia lathyrus* plant material was chopped and ground in a blender for about 10 minutes with 500 cc of cyclohexane at 22° C. The resulting mixture was filtered to remove solids, and the cyclohexane solution collected and evaporated under vacuum leaving a hydrocarbon resin. A yield of 0.6% hydrocarbon based on the initial substrate weight was obtained.

EXAMPLE II

The following simulates a batch process for recovery of hydrocarbons from latex-containing plants with the use of enzymes.

A 33.2 g portion of *Euphorbia lathyrus* plant material was chopped, ground and added to a 500 cc reactor which previously had been charged with 0.37 g Miles Laboratories Takamine (Trademark) Brand Developmental *Trichoderma viride* Cellulase Concentrate and 0.05 g Rohm and Haas Rhozyme HP-150 (Trademark) Concentrate hemicellulase, in 250 cc of an acetic acid/sodium acetate solution buffered at pH 5.0. The reaction was vigorously stirred for a period of 24 hours at 45° C., after which it was cooled to 22° C. The entire reaction mixture was then extracted with four 125 cc portions of reagent grade cyclohexane. The cyclohexane fractions were then separated and recombined and the resulting solution evaporated under vacuum to obtain a hydrocarbon resin. The yield of hydrocarbon resin was 2.4% based on the initial substrate weight. Yield accordingly was 400% greater than the yield obtained by the process of Example I.

EXAMPLE III

In the procedure of Example I, 35.3 g *Euphorbia marginata* was treated. Yield of hydrocarbon resin was 0.8% based on initial substrate weight.

EXAMPLE IV

In the procedure of Example II, 35.2 g *Euphorbia marginata* was treated. Yield of hydrocarbon resin was 1.4% based on initial plant weight. Yield was accordingly 160% greater than in Example III.

EXAMPLES V-VI

In the procedure of Example II but using an acetone solvent, a number of hydrocarbon-containing plants were treated. Temperature was 50° C. Time of reaction was 2 hours. 2 g of enzyme was used in each run. Details are in Table I.

TABLE I

| | Hydrocarbon Recovery-Enzyme Treatment | | | |
| | | | Hydrocarbon Resin Yield, | |
| Example | Plant | Enzyme | Fresh* Wt % | Dry** Wt % |
| --- | --- | --- | --- | --- |
| V | A. syriaca | None | 3.0 | 15.2 |
| | A. syriaca | A | 2.9 | 14.8 |
| | A. syriaca | B | 4.0 | 22.5 |
| | A. syriaca | C | 3.8 | 21.1 |
| | A. syriaca | B | 4.1 | 19.9 |

TABLE I-continued

| | Hydrocarbon Recovery-Enzyme Treatment | | | |
| | | | Hydrocarbon Resin Yield, | |
| Example | Plant | Enzyme | Fresh* Wt % | Dry** Wt % |
| --- | --- | --- | --- | --- |
| VI | E. tirucalli | None | 2.1 | 16.1 |
| | E. tirucalli | A | 2.4 | 17.9 |
| | E. tirucalli | B | 4.2 | 29.2 |
| | E. tirucalli | C | 2.2 | 19.3 |
| | E. tirucalli | B | 4.3 | 39.2 |

A - Pectinol R-10, (Trademark) Rohm & Haas Co.
B - Pectinol 10-M, (Trademark) Rohm & Haas Co.
C - Rhozyme HP-150, (Trademark) Rohm & Haas Co.
*Based on fresh weight of material
**Based on dry weight of material

EXAMPLE VII

In the procedure of Example II, 71.05 g of *E. tirucalli* was refluxed in actone. Control without any enzyme was refluxed for 20 hours. 123.7 g *E. tirucalli* in 2.0 g Pectinol 10-M (Trademark) enzyme was refluxed for 4 hours. Results are in Table II.

TABLE II

| | Hydrocarbon Recovery-*tirucalli* | | |
| | | Hydrocarbon Yield, | |
| | Enzyme Wt. % | Fresh* Wt. % | Dry** Wt. % |
| --- | --- | --- | --- |
| Control | 0 | 2.3 | 20.0 |
| E. tirucalli | 2.0 | 4.1 | 31.3 |

*Based on fresh weight of material
**Based on dry weight of material

EXAMPLE VIII

The procedure of Example II was repeated using other hydrocarbon-containing plants and cyclohexane as the extracting solvent. 2.0 g of enzyme were added to plant material in each case. Results are in Table III.

TABLE III

| Hydrocarbon Recovery-Enzyme Treatment | | | | | |
| | | | | Yield wt. % | |
| Plant | Plant Source | Enzyme | Reaction Time-Hrs | Before Drying | Dry |
| --- | --- | --- | --- | --- | --- |
| E. marginata | Fz | None | 0 | 0.8 | 4.3 |
| E. marginata | Fz | E | 24 | 1.3 | 8.9 |
| E. marginata | Fz | F | 24 | 1.4 | 7.4 |
| G. squarrosa | Fz | None | 0 | — | 15.1 |
| G. squarrosa | Fz | F | 12 | — | 25.6 |
| E. heterophylla | Fz | None | 0 | 1.8 | 7.9 |
| E. heterophylla | Fz | F | 12 | 4.2 | 16.6 |
| A. syriaca | Fr | None | 0 | 1.2 | 6.2 |
| A. syriaca | Fr | F | 12 | 3.9 | 17.8 |
| E. esula | Fz | None | 0 | 0.9 | 3.2 |
| E. esula | Fz | F | 12 | 2.1 | 7.1 |
| A. tuberosa | Fz | None | 0 | 1.5 | 6.1 |
| A. tuberosa | Fz | F | 12 | 3.3 | 15.3 |
| C. procera | Fr | None | 0 | 1.2 | 7.9 |
| C. procera | Fr | F | 12 | 2.1 | 14.9 |
| E. lathyrus | Gr | None | 0 | 0.6 | 4.7 |
| E. lathyrus | Gr | None | 12 | 0.6 | 1.3 |
| E. lathyrus | Gr | F | 6 | 3.4 | 5.8 |
| E. lathyrus | Gr | F | 12 | 4.2 | 8.6 |
| E. lathyrus | Gr | F | 24 | 4.8 | 9.4 |
| E. lathyrus | Gr | F | 24 | 2.3 | 18.8 |
| E. lathyrus | Fz | F | 24 | 2.4 | 17.8 |
| E. lathyrus | Fz | E | 24 | 0.9 | 4.1 |
| E. lathyrus | Fz | G | 24 | 1.2 | 2.9 |
| E. lathyrus | Fz | F | 12 | 3.3 | 8.4 |
| E. lathyrus | Fz | None | 72 | 1.2 | 3.2 |
| E. lathyrus | Fz | F | 72 | 1.2 | 8.7 |

TABLE III-continued

Hydrocarbon Recovery-Enzyme Treatment

| Plant | Plant Source | Enzyme | Reaction Time-Hrs | Yield wt. % Before Drying | Dry |
|---|---|---|---|---|---|
| E. lathyrus | Fz | F | 72 | 3.9 | 22.3 |
| E. tirucalli | Gr | E | 24 | 0.7 | 3.5 |
| E. tirucalli | Gr | F | 24 | 2.2 | 12.9 |

Notes:
Fz - frozen, field-grown
Fr - fresh, field-grown
Gr - greenhouse grown
G - Rhozyme HP150 (Trademark) (Rohm & Haas Co.)
F - Takamine (Trademark) Brand TVC Concentrate and Rhozyme HP150 (Trademark) (Rohm & Haas Co.)
E - Takamine (Trademark) Brand TV Concentrate (Miles Laboratories)

What is claimed is:

1. A process using enzymes for enzymatically converting whole plant biomass containing hydrocarbon-containing plants selected from the Euphorbiaceae, Apocynaceae, Asclepiadaceae, Compositae, Cactaceae and Pinaceae families and mixtures thereof to soluble sugars and recovering hydrocarbons from said plants in increased yields which comprises:
   (a) hydrolyzing said whole plant biomass in the presence of enzymes selected from the group consisting of cellulase, hemicellulase and mixtures thereof under conditions which promote conversion of cellulose and hemicellulose to soluble sugars;
   (b) removing a stream of hydrolysis products comprising a liquid sugar-containing phase, a liquid hydrocarbon-containing phase and a solid phase containing unhydrolyzed spent solids, all phases containing enzymes selected from the group consisting of cellulase and hemicellulase enzymes and mixtures thereof from the hydrolysis stage;
   (c) separating liquid phases and solid phases of step (b);
   (d) continuously adding a stream to step (a) of fresh said whole plant biomass to replenish said whole plant biomass converted to hydrolysis products;
   (e) separating said liquid phases from step (c) thereby recovering said enzymes present and said hydrocarbons present;
   (f) recovering a stream of product sugar solution and enzyme solution from step (e);
   (g) sterilizing a sugar product stream from step (f) to serve as sterile growth medium for microorganisms;
   (h) adding the recovered solids from step (c) to the hydrolysis stage;
   (i) providing a stream of makeup enzymes selected from the group consisting of cellulase, hemicellulase and mixtures thereof for the hydrolysis steps by the steps including:
      (1) in a first zone, growing in a suitable medium enzyme-synthesizing organisms selected from the group consisting of cellulase-synthesizing microorganisms, hemicellulase-synthesizing microorganisms and mixtures thereof, said microorganism-containing medium comprising minor portions of the product solutions;
      (2) in a second zone contacting said microorganism-containing medium with an amount of cellulosic and hemicellulosic materials in an amount sufficient to induce formation of cellulase and hemicellulase under conditions substantially nonsupportive of growth of the cellulase and hemicellulase-secreting microorganisms.

2. The process of claim 1 wherein said whole plant biomass comprises hydrocarbon-containing plants selected from the group consisting of *Euphorbia heterophylla, Euphorbia lathyrus, Euphorbia marginata, Euphorbia tirucalli, Ascelpias syriaca, Calotropis procera, Parthenium argentatum, Apocynum sibiricum* and mixtures thereof.

3. The process of claim 1 wherein said enzymes comprise enzymes from the microorganisms *Trichoderma viride, Aspergillus niger, Basidiomycetes poria, Trichoderma koningii, Fusarium soloni, Clostriduim thermocellum, Fusarium javanicum* and mixtures thereof.

4. The process of claim 1 wherein the said process is a batch process.

5. The process of claim 1 wherein the said process is a continuous process.

* * * * *